United States Patent
Sutermeister et al.

(10) Patent No.: US 9,242,073 B2
(45) Date of Patent: Jan. 26, 2016

(54) ELECTRICALLY ACTUATED ANNELID

(75) Inventors: Derek Sutermeister, Plymouth, MN (US); Jay Rassat, Buffalo, MN (US); Dan Wefel, Fridley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2527 days.

(21) Appl. No.: 11/506,491

(22) Filed: Aug. 18, 2006

(65) Prior Publication Data

US 2008/0125706 A1 May 29, 2008

(51) Int. Cl.
*A61M 31/00* (2006.01)
*A61M 25/01* (2006.01)
*A61M 25/00* (2006.01)

(52) U.S. Cl.
CPC ........... *A61M 25/0116* (2013.01); *A61M 31/00* (2013.01); *A61M 2025/0058* (2013.01)

(58) Field of Classification Search
CPC .............. A61B 1/0053; A61B 1/00156; A61B 1/0051; A61B 2017/003; A61B 1/005; A61B 1/008; A61M 25/0116; A61M 25/0147; A61M 25/0155; A61M 25/1011; A61M 2025/0058; A61M 25/0122; A61M 2025/015; A61M 2025/0161; A61F 2/958
USPC ........ 604/95.01, 95.03, 95.05, 104, 510, 531, 604/95.02, 95.04, 96.01, 101.01, 101.05; 128/203.28; 623/1.11, 1.23; 606/200
See application file for complete search history.

(56) References Cited

U.S. PATENT DOCUMENTS

| | | | | |
|---|---|---|---|---|
| 2,078,686 A | * | 4/1937 | Rowe | 604/103.02 |
| 3,485,237 A | * | 12/1969 | Bedford | 600/581 |
| 3,895,637 A | * | 7/1975 | Choy | 604/95.03 |
| 4,176,662 A | * | 12/1979 | Frazer | 600/114 |
| 4,207,872 A | * | 6/1980 | Meiri et al. | 600/116 |
| 4,389,208 A | * | 6/1983 | LeVeen et al. | 604/95.03 |
| 4,690,131 A | * | 9/1987 | Lyddy et al. | 600/115 |
| 4,838,859 A | * | 6/1989 | Strassmann | 604/95.03 |
| 4,848,168 A | * | 7/1989 | Negishi | 73/865.8 |
| 5,090,259 A | * | 2/1992 | Shishido et al. | 73/866.5 |
| 5,144,848 A | * | 9/1992 | Uenishi et al. | 73/866.5 |
| 5,152,748 A | * | 10/1992 | Chastagner | 604/95.05 |
| 5,337,732 A | * | 8/1994 | Grundfest et al. | 600/116 |
| 5,386,741 A | * | 2/1995 | Rennex | 74/490.05 |
| 5,398,670 A | * | 3/1995 | Ortiz et al. | 600/114 |

(Continued)

FOREIGN PATENT DOCUMENTS

EP    1 747 749    1/2007
WO   WO 9628841   9/1996

(Continued)

OTHER PUBLICATIONS

Zhou et al., "Actuators for The Cochlear Implant", Synthetic Metals vol. 135-136 (2003) pp. 39-40.

(Continued)

*Primary Examiner* — David C Eastwood
*Assistant Examiner* — Erin Colello
(74) *Attorney, Agent, or Firm* — Seager, Tufte & Wickhem LLP

(57) ABSTRACT

An apparatus for delivery through a vessel including an extensor segment and first and second anchor segments positioned on either side of the extensor segment, wherein each segment has associated with it an individually-addressable electroactive polymer.

20 Claims, 11 Drawing Sheets

(56) References Cited

U.S. PATENT DOCUMENTS

| | | | |
|---|---|---|---|
| 5,405,322 A * | 4/1995 | Lennox et al. | 606/28 |
| 5,415,633 A * | 5/1995 | Lazarus et al. | 604/95.05 |
| 5,645,520 A * | 7/1997 | Nakamura et al. | 600/151 |
| 5,662,587 A * | 9/1997 | Grundfest et al. | 600/114 |
| 5,821,666 A * | 10/1998 | Matsumoto et al. | 310/316.01 |
| 5,827,304 A * | 10/1998 | Hart | 606/159 |
| 5,855,565 A | 1/1999 | Bar-Cohen et al. | |
| 5,868,708 A * | 2/1999 | Hart et al. | 604/104 |
| 5,906,591 A * | 5/1999 | Dario et al. | 604/95.03 |
| 6,103,399 A | 8/2000 | Smela et al. | |
| 6,249,076 B1 | 6/2001 | Madden et al. | |
| 6,278,084 B1 * | 8/2001 | Maynard | 219/209 |
| 6,514,237 B1 * | 2/2003 | Maseda | 604/533 |
| 6,679,836 B2 * | 1/2004 | Couvillon, Jr. | 600/146 |
| 6,749,556 B2 | 6/2004 | Banik | |
| 6,764,441 B2 * | 7/2004 | Chiel et al. | 600/115 |
| 6,770,027 B2 * | 8/2004 | Banik et al. | 600/146 |
| 6,809,462 B2 | 10/2004 | Pelrine et al. | |
| 6,812,624 B1 * | 11/2004 | Pei et al. | 310/309 |
| 6,835,173 B2 * | 12/2004 | Couvillon, Jr. | 600/146 |
| 6,872,433 B2 * | 3/2005 | Seward | A61L 29/126 428/35.7 |
| 6,921,360 B2 | 7/2005 | Banik | |
| 6,933,659 B2 * | 8/2005 | Krogh et al. | 310/330 |
| 6,939,291 B2 * | 9/2005 | Phee Soo Jay et al. | 600/114 |
| 6,940,211 B2 | 9/2005 | Pelrine et al. | |
| 6,960,163 B2 * | 11/2005 | Ewers et al. | 600/114 |
| 6,969,395 B2 | 11/2005 | Eskuri | |
| 6,982,514 B1 | 1/2006 | Lu et al. | |
| 6,991,616 B2 * | 1/2006 | Bencini et al. | 604/95.01 |
| 6,997,870 B2 | 2/2006 | Couvillon, Jr. | |
| 7,169,166 B2 * | 1/2007 | Richter | 606/200 |
| 7,635,345 B2 * | 12/2009 | Gross et al. | 604/99.01 |
| 7,635,346 B2 * | 12/2009 | Cabiri et al. | 604/99.01 |
| 7,645,290 B2 * | 1/2010 | Lucas | 606/159 |
| 7,798,992 B2 * | 9/2010 | Ortiz | A61B 1/00082 604/106 |
| 8,517,923 B2 * | 8/2013 | Belson et al. | 600/146 |
| 2002/0035346 A1 | 3/2002 | Reynolds et al. | |
| 2002/0054060 A1 | 5/2002 | Schena | |
| 2002/0130673 A1 | 9/2002 | Pelrine et al. | |
| 2003/0065250 A1 * | 4/2003 | Chiel et al. | 600/115 |
| 2003/0181856 A1 * | 9/2003 | Goldman | 604/103.01 |
| 2004/0008853 A1 | 1/2004 | Pelrine et al. | |
| 2004/0068161 A1 | 4/2004 | Couvillon, Jr. | |
| 2004/0068220 A1 | 4/2004 | Couvillon, Jr. et al. | |
| 2004/0068224 A1 | 4/2004 | Couvillon, Jr. et al. | |
| 2004/0087982 A1 | 5/2004 | Eskuri | |
| 2004/0143160 A1 | 7/2004 | Couvillon, Jr. | |
| 2005/0049671 A1 * | 3/2005 | Wang et al. | 623/1.12 |
| 2005/0065500 A1 | 3/2005 | Couvillon, Jr. et al. | |
| 2005/0085693 A1 * | 4/2005 | Belson et al. | 600/146 |
| 2005/0102017 A1 | 5/2005 | Mattison | |
| 2005/0107669 A1 | 5/2005 | Couvillon, Jr. | |
| 2005/0165439 A1 * | 7/2005 | Weber et al. | 606/191 |
| 2005/0267561 A1 * | 12/2005 | Jones et al. | 623/1.11 |
| 2006/0025813 A1 | 2/2006 | Shelton et al. | |
| 2006/0041264 A1 | 2/2006 | Eskuri | |
| 2006/0047302 A1 | 3/2006 | Ortiz et al. | |
| 2006/0047303 A1 | 3/2006 | Ortiz et al. | |
| 2006/0069425 A1 * | 3/2006 | Hillis et al. | 623/1.16 |
| 2006/0089533 A1 * | 4/2006 | Ziegler et al. | 600/114 |
| 2006/0111618 A1 | 5/2006 | Couvillon, Jr. | |
| 2006/0253145 A1 * | 11/2006 | Lucas | 606/159 |
| 2006/0271151 A1 * | 11/2006 | McGarry et al. | 623/1.11 |
| 2007/0010868 A1 * | 1/2007 | Ferren et al. | 623/1.15 |
| 2007/0038237 A1 * | 2/2007 | Swayze et al. | 606/191 |
| 2007/0066929 A1 * | 3/2007 | Ferren et al. | 604/8 |
| 2007/0106302 A1 * | 5/2007 | Ortiz | 606/108 |
| 2007/0156211 A1 * | 7/2007 | Ferren et al. | 607/101 |
| 2007/0250036 A1 * | 10/2007 | Volk et al. | 604/510 |
| 2008/0004595 A1 * | 1/2008 | Viswanathan et al. | 604/500 |
| 2008/0097292 A1 * | 4/2008 | Cabiri et al. | 604/95.01 |

FOREIGN PATENT DOCUMENTS

| | | |
|---|---|---|
| WO | WO 0078222 | 12/2000 |
| WO | WO 03/030727 | 4/2003 |
| WO | WO 03039859 | 5/2003 |
| WO | WO 2004092050 | 10/2004 |

OTHER PUBLICATIONS

Jager et al. "Microfabricating Conjugated Polymer Actuators", Science 290, pp. 1540-1545 (2000).

Madden et al., "Polypyrrole Actutators: Modeling and Performance", Smart Sturctures and Materials (2001) pp. 72-83.

Smela et al., "Electrochemically Driven Polypyrrole Bilayers for Moving and Positioning Bulk Micromachined Silicon Plates", Journal of Micromechanical Systems vol. 8, No. 4 (Dec. 1999) pp. 373-383.

Smela et al., "Thiol-Modified Pyrrole Monomers: 1. Synthesis, Characterization, and Polymerization of 1-(2-Thioethyl)pyrrole and 3-(2-Thioethyl)pyrrole", Langmuir (1998), pp. 2970-2975.

A.B. Slatkin et al., "The Development of a Robotic Endoscope," Aug. 5, 1995, Proceedings 1995 IEE/RSJ International Conference on Intelligent Robots and Systems: Human Robot Interaction and Cooperative Robots, Pittsburgh, PA., Aug. 5-9, 1995, pp. 162-171.

* cited by examiner

ELECTRICALLY ACTUATED ANNELID

FIELD OF DISCLOSURE

This application relates to electro-active polymers for medical applications.

BACKGROUND

Catheter systems have been used for internal delivery of treatment devices and drugs. Such systems have been used with minimally invasive surgical procedures, such as keyhole surgery.

Current catheter systems often use guide wires to position the treatment devices and drugs within the body. Effective use of current systems requires some skill to maneuver the guide wire with accuracy and precision.

Electro-active polymers can be used in devices that can exert forces or execute movements upon external stimulation, e.g., electrical current. Electrical current causes relative volume change of the electro-active polymer resulting in movements such as bending, expanding or contracting. Some are made of a bi-layer of a conducting polymer and a carrier substrate, e.g., a metal or a polymer. These devices can have lateral dimensions ranging from micrometers to centimeters and layer thickness in the range of nanometers to millimeters. Additional information concerning electro-active polymers and their application are described in International Publication Nos. WO 96/28841, filed Aug. 3, 1996; WO 00/78222, filed Jun. 18, 2000; WO 03/39859, filed Jun. 11, 2002; and WO 04/92050, filed Apr. 8, 2004, and U.S. Pat. No. 6,103, 399, filed Dec. 30, 1997 and issued Aug. 25, 2000; and U.S. Pat. No. 6,933,659, filed May 5, 2004 and issued Aug. 23, 2005, all of which are incorporated herein by reference.

SUMMARY

In one aspect, an apparatus for delivery through a vessel includes an extensor segment, and first and second anchor segments positioned on either side of the extensor segment, wherein each segment has associated with it an individually-addressable electro-active polymer.

Implementations can include one or more of the following. At least one of the segments is configured to carry an agent. The apparatus includes a power source coupled to provide electrical current to actuate the electro-active polymer of each segment. The apparatus includes a controller configured to direct a control signal to cause actuation of the electro-active polymer associated with a segment. The electro-active polymer includes a polypyrrole polymer. The electro-active polymer associated with a segment includes an individually-addressable bulk-actuating electro-active polymer. The electro-active polymer associated with a segment includes an individually-addressable length-actuating electro-active polymer. A segment includes a pair of electro-active polymer fingers configured to form a fork in response to actuation. A segment includes a series of sub-segments, wherein each sub-segment has associated with it an individually-addressable electro-active polymer. The extensor segment includes plural ligaments, wherein each ligament has associated with it an individually-addressable electro-active polymer. A segment includes a pair of individually-addressable electro-active sides configured to change the orientation of the segment in response to actuation. The extensor segment includes plural individually addressable ligaments wound in a helix. At least one segment includes a separately actuable agent-holding electro-active polymer configured to secure the agent in response to actuation. At least one of the segments includes a radio-opaque material. The apparatus includes an external power source electrically coupled to the segments. The electrical coupling can be an inductive coupling. The apparatus includes a battery electrically coupled to the segments.

In another aspect, a method of propelling an apparatus through a vessel includes securing a first anchor segment within the vessel, elongating an extensor segment, securing a second anchor segment within the vessel, releasing the first anchor segment from the vessel, and contracting the extensor segment.

Implementations can include one or more of the following. The method includes steering the apparatus within the vessel. The method includes extending a first side of an anchor segment while contracting a second side of the anchor segment. The method includes controlling the speed of propulsion. The method includes controlling the direction of propulsion. The method includes affixing an agent to a segment of the delivery apparatus.

In yet another aspect a synthetic annelid includes a plurality of connected segments, each segment being actuable independently of the other segments.

Implementations can include a segment having associated with it an electro-active polymer.

DETAILED DESCRIPTION

Figure 1:
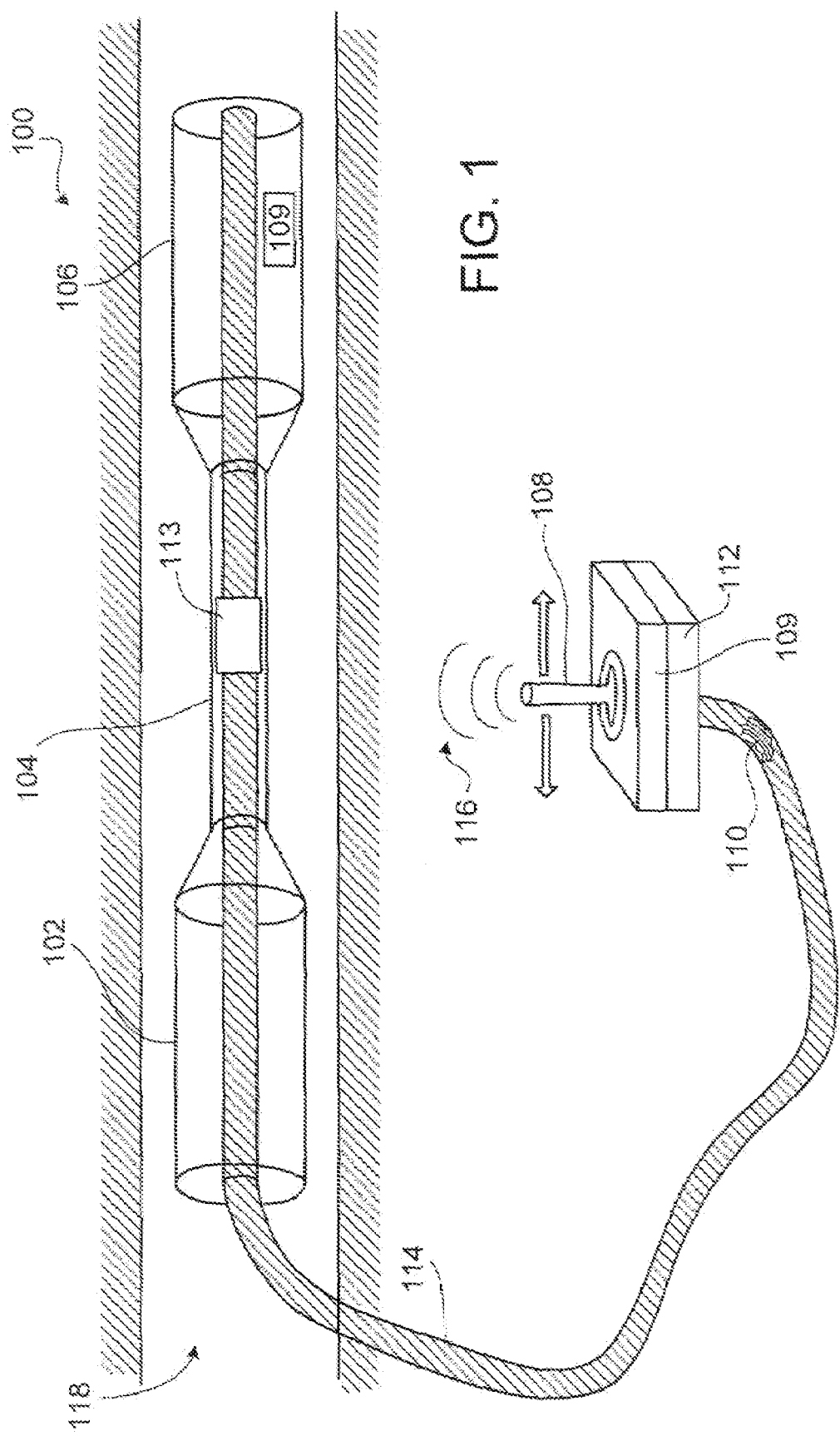
FIG. 1 shows a synthetic annelid and control system.

In the example of FIG. 1, a synthetic annelid 100 has first and second anchor segments 102, 106 on either side of a center extensor segment 104. Together, the anchor segments 102, 106 and the extensor segment 104 cooperate to allow the annelid 100 to crawl through a network of vessels. In some implementations, the annelid 100 delivers agents into a body to a position that might otherwise be unreachable. In other implementations, the device contains radio-opaque materials to allow the user to visualize the annelid as it traverses the network.

As used in this description, vessels include arteries or veins, as well as pipes and tubes generally. Agents refer to drugs or medical devices such as stents, balloons, grafts, or filters, as well as non-medical tools generally. Bodies include the human body or animal bodies, as well as physical objects generally.

Incorporated into the anchor segments 102, 106 and the extensor segment 104 is an electro-active polymer (EAP), for example, a polypyrrole polymer.

The user applies an electrical current to the EAPs to activate or "actuate" the segments 102, 104, 106 to manipulate the mass, size, shape or orientation of the segments from a preset condition, thereby causing the annelid 100 to crawl through a vessel, as discussed in more detail in connection with FIGS. 2-6. The user selectively actuates the EAPs with an external joystick 108 to electronically control both the direction and speed of the annelid 100 as it crawls through the vessel. The joystick 108 interacts with a controller 109 that selectively directs electrical current to the segments 102, 104, 106, thereby actuating the segments to cause movement. For example, the user taps the joystick 108 in the proximal or distal direction to cause the annelid 100 to slowly crawl proximally or distally, respectively. The user pushes the joystick 108 in the proximal or distal direction to cause the annelid 100 to crawl more quickly proximally or distally, respectively. The controller 109 can be disposed either external to the annelid or integrated in the annelid.

In some implementations, the controller 109 directs the electrical current to the segments 102, 104, 106 via electrical wires 110 that extend through a micro-catheter 114 between the segments 102, 104, 106 and a power source 112. In other implementations, the power source is an external power source 112. The external power source 112 can be integrated with the joystick 108 so that current is transmitted to the annelid 100 on a wire. Alternatively, the external power source can be an induction power source that induces current in the annelid 100. This induces a current in the annelid 100 that either actuates the segments, or charges a battery that provides power for actuating the segments. The annelid 100 can therefore be powered without electrical wires 110.

In yet other implementations, the power source is a battery. The use of a battery 113 as a power source also eliminates the need for having a length of electrical wire 110 extending all the way from the annelid 100 through the micro-catheter 114. Some implementations feature both a battery powered system and an external power supply to serve as a backup power system.

Figure 2:
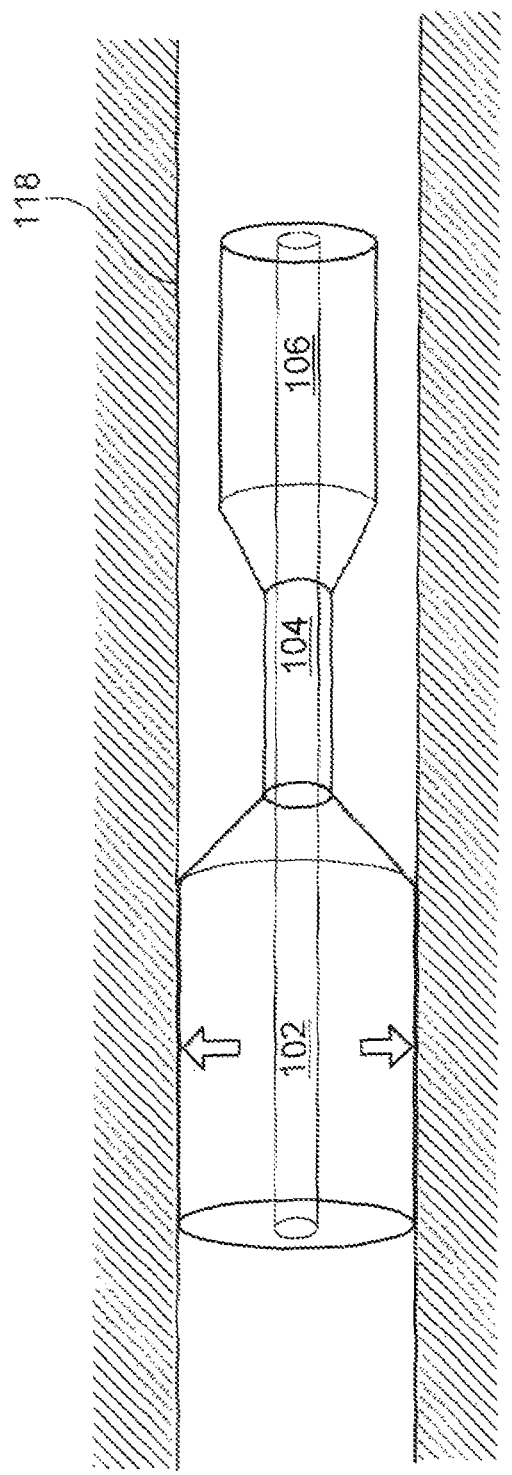
FIGS. 2-6 show a movement of the annelid.
Figure 3:
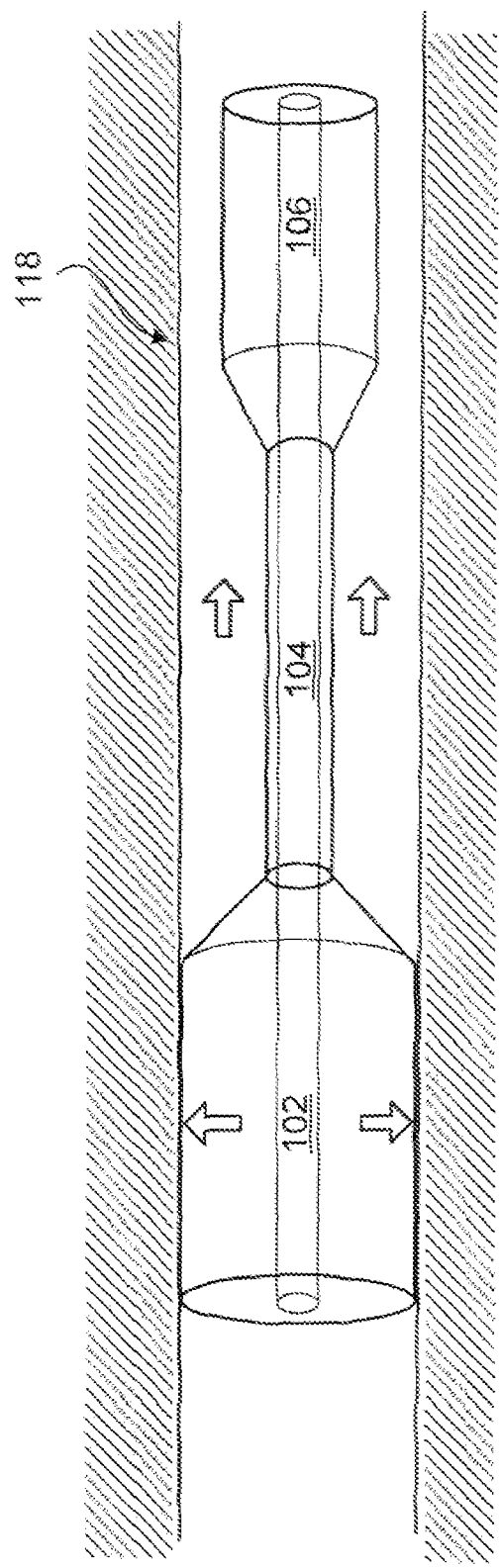
Figure 4:
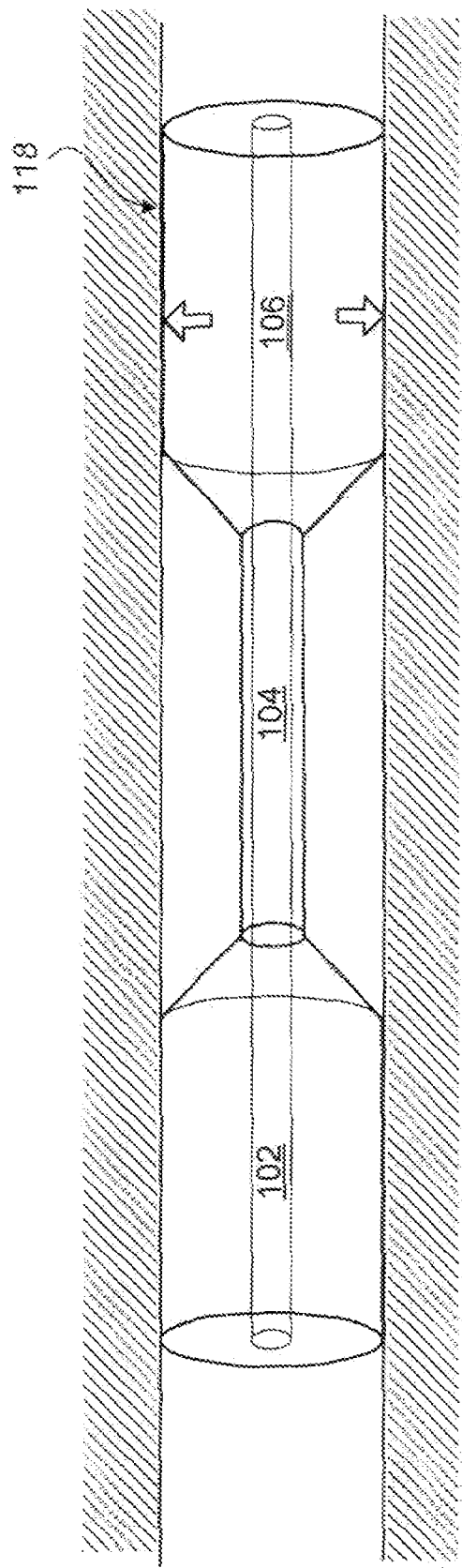
Figure 5:
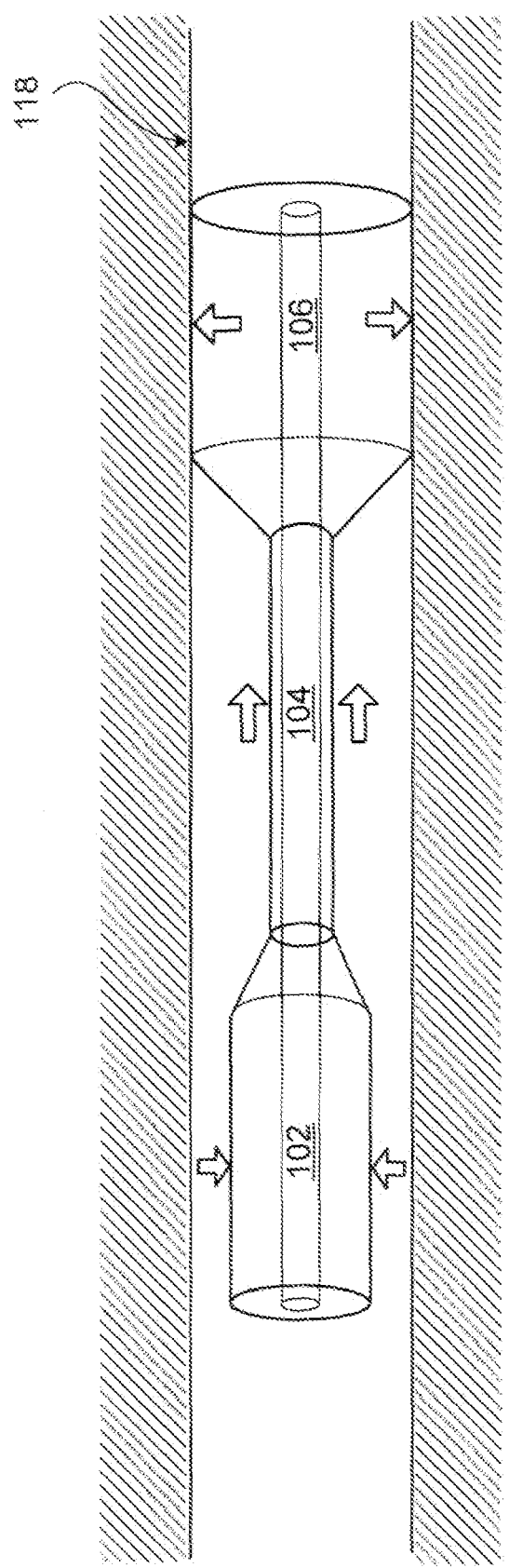
Figure 6:
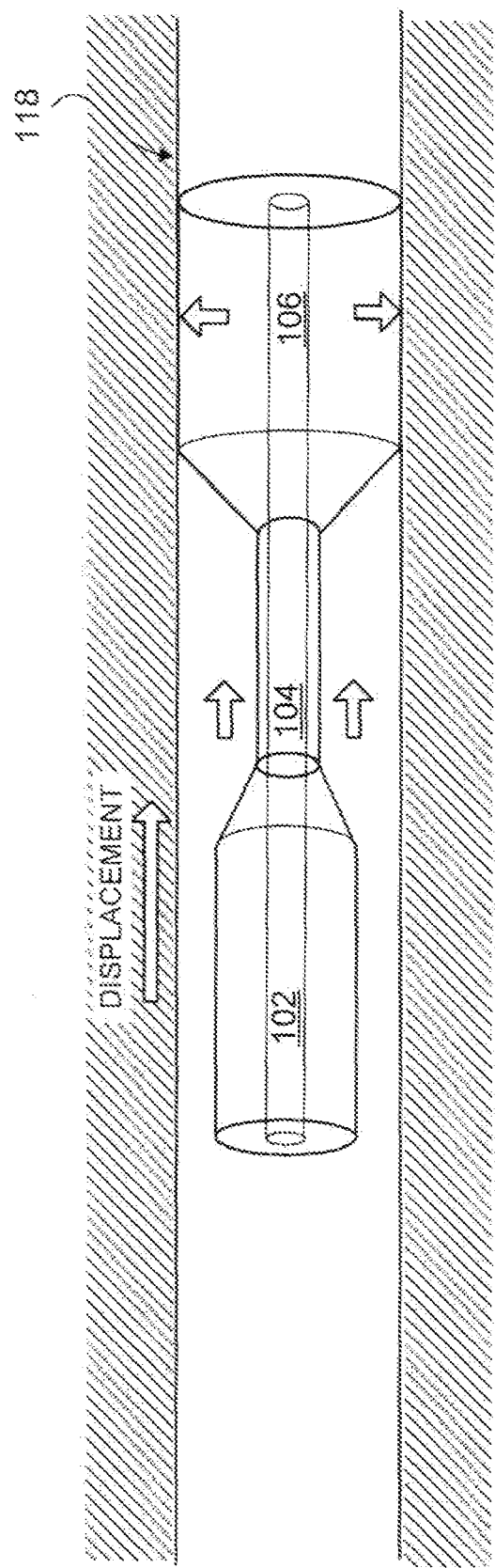

The user selectively actuates the segments 102, 104, 106 to cause the annelid 100 to crawl through the network of vessels. In the example of FIGS. 1-6, after having positioned the annelid 100 within the vessel 118 (FIG. 1), the user actuates the first anchor segment 102 (FIG. 2). The first anchor segment 102, when actuated, enlarges its diameter. This places the adjacent area of the vessel under tensile or compressive load and secures the annelid 100. The user then actuates the extensor segment 104, as shown in FIG. 3. The extensor segment 104, when actuated, elongates the annelid 100. The user then actuates the second anchor segment 106, as shown in FIG. 4. Like the first anchor segment 102, the second anchor segment 106, when actuated, enlarges its diameter, thereby placing the adjacent area of the vessel under a tensile or compressive load and securing the annelid 100. The user then deactuates the first anchor segment 102 (FIG. 5) to deanchor it, and deactuates the extensor segment 104, as shown in FIG. 5. As a result, as shown in FIG. 6, the device is displaced by a distance that depends on the extent to which the extensor segment 104 was elongated. By deactuating the second anchor segment 106 and then repeating the actuating sequence shown in FIGS. 2-6, the user causes the annelid 100 to crawl proximally. By reversing the steps of FIGS. 2-6, the user can also cause the annelid 100 to crawl distally. This manner of causing the annelid to traverse the network of vessels may eliminate the need for guide wires or guide catheters in applications where they are traditionally used.

In some implementations, the segments 102, 104, 106 each have a series of individually addressable actuating sub-segments to allow the annelid 100 to crawl through the vessel on a finely controlled basis. These implementations permit the user to cause minute movements of one sub-segment of the annelid 100 without affecting other sub-segments of the annelid.

Figure 7:
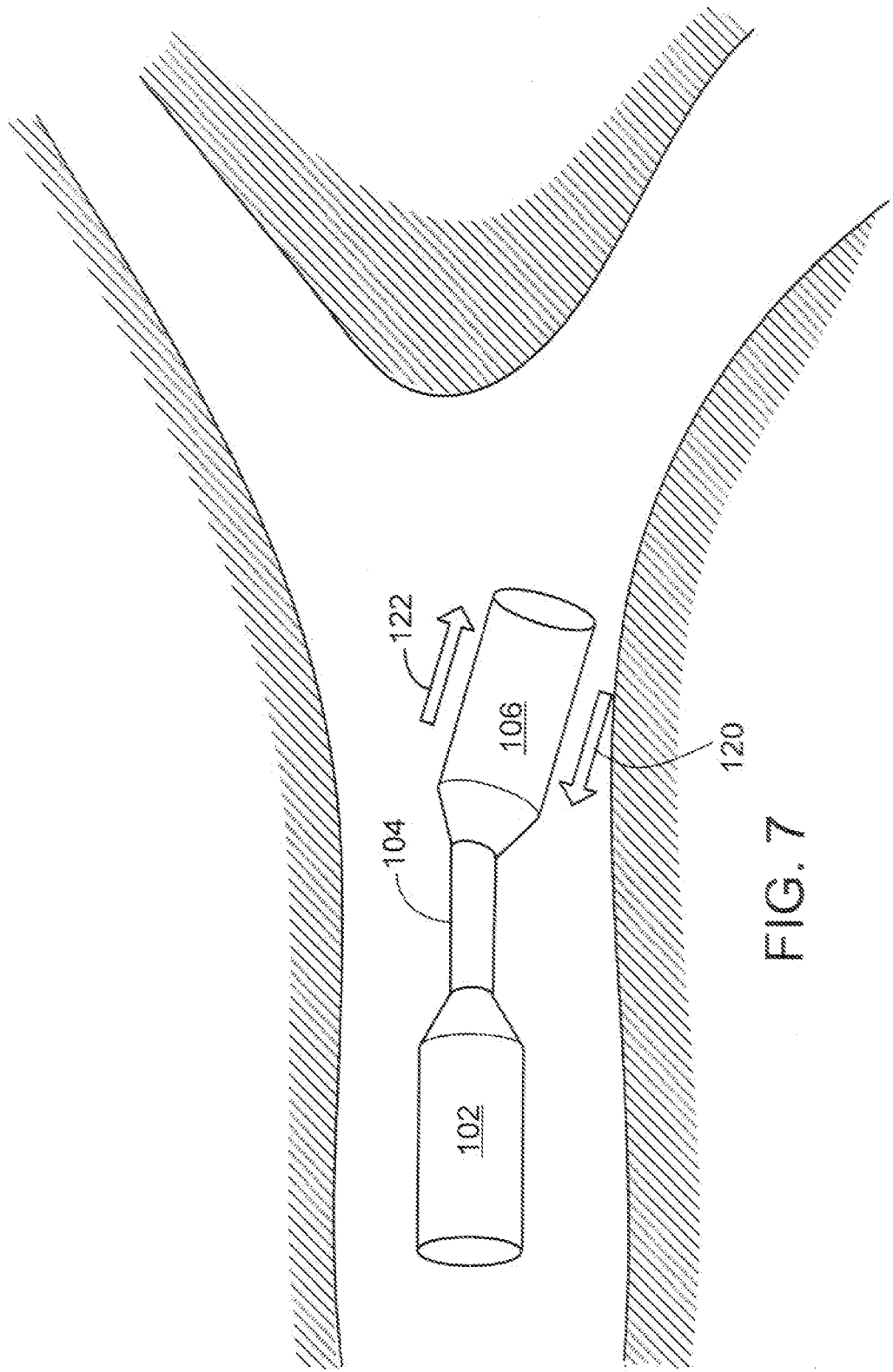
FIGS. 7-8 show anchoring mechanisms for the annelid.

In an embodiment shown in FIG. 7, the user actuates opposed first and second sides 120, 122 of the anchor segment 106 to contract the first side 120 and elongate the second side 122 of the anchor segment 106. As a result, the user changes the orientation of the anchor segment, thereby essentially steering the annelid 100. In addition, in this implementation, by changing the orientation of the anchor segments 102, 106, the user can direct the annelid 100 through a particular branch of a fork (i.e. an intersection of paths) in the vessel.

Figure 8:
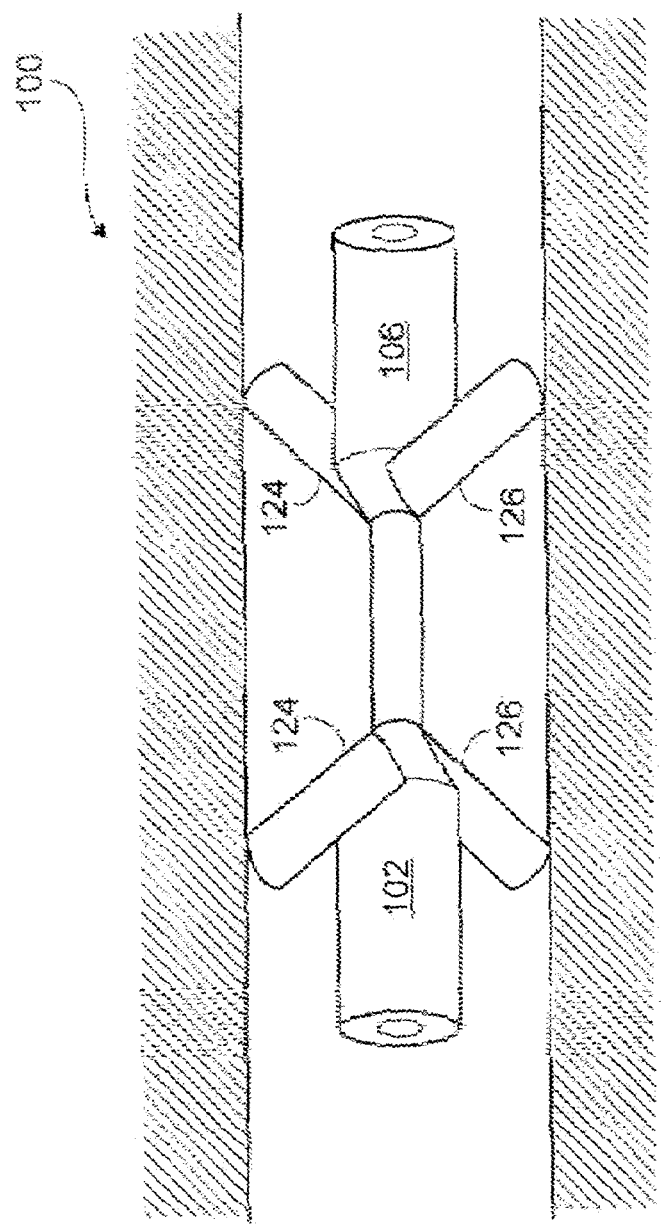

In another embodiment shown in FIG. 8, the anchor segments 102, 106 feature individually actuable fingers 124, 126. When actuated, the fingers 124, 126 change orientation (as described above) to swing out and form a fork-like structure that secures the annelid 100 to the vessel wall.

Figure 9:
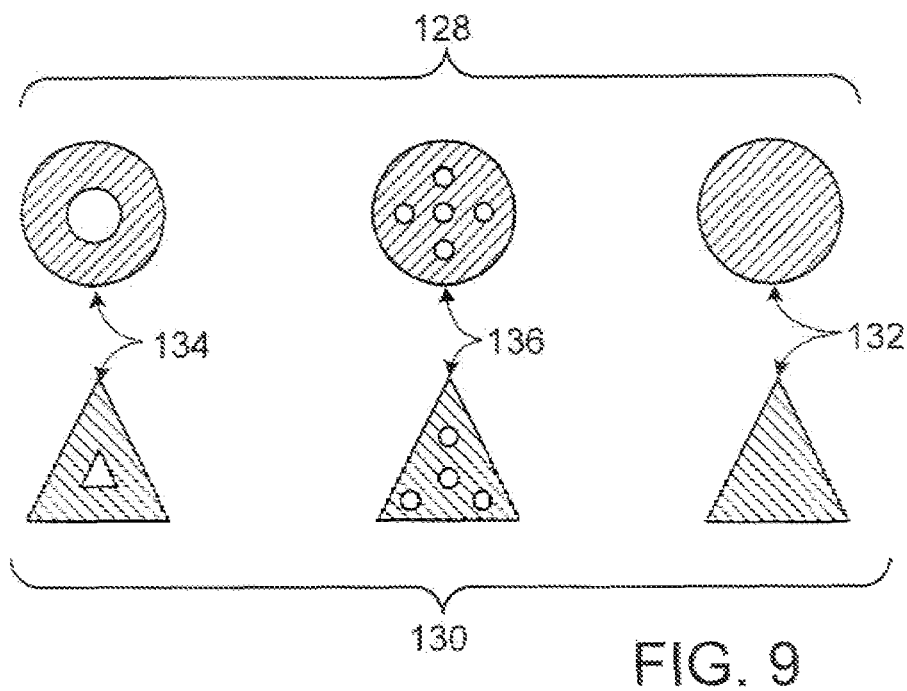
FIG. 9 shows cross-sectional views of constructions of an anchor segment of the annelid.

The anchor segments 102, 106 can, but need not have identical structural cross-sections. While the anchor segments 102, 106 can be of any cross-section, FIG. 9 shows possible cross-sections, including circular cross-sections 128 and triangular cross-sections 130. In either case, as shown in FIG. 9, the cross-sections can be solid 132, or with one hole 134 or with many holes 136. In some implementations, to facilitate blood flow through the vessel, the cross-section has one or more holes.

Figure 10:
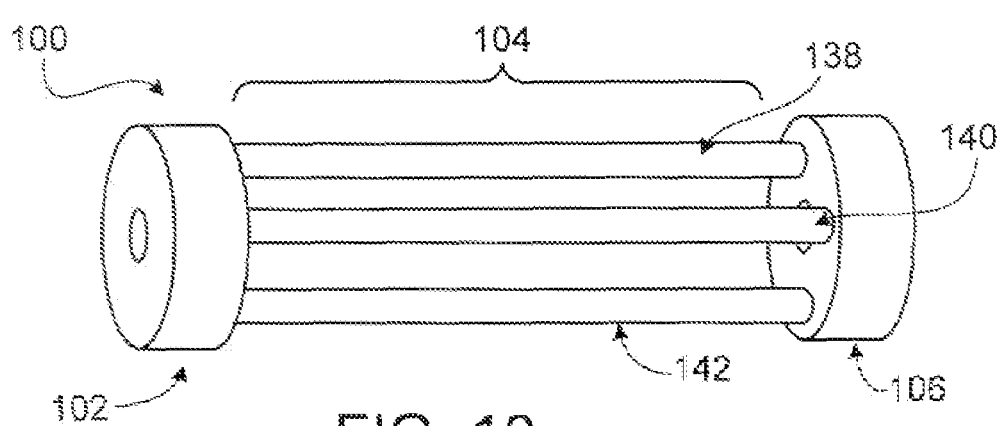
FIGS. 10-11 show constructions of an extensor segment of the annelid.
Figure 11:
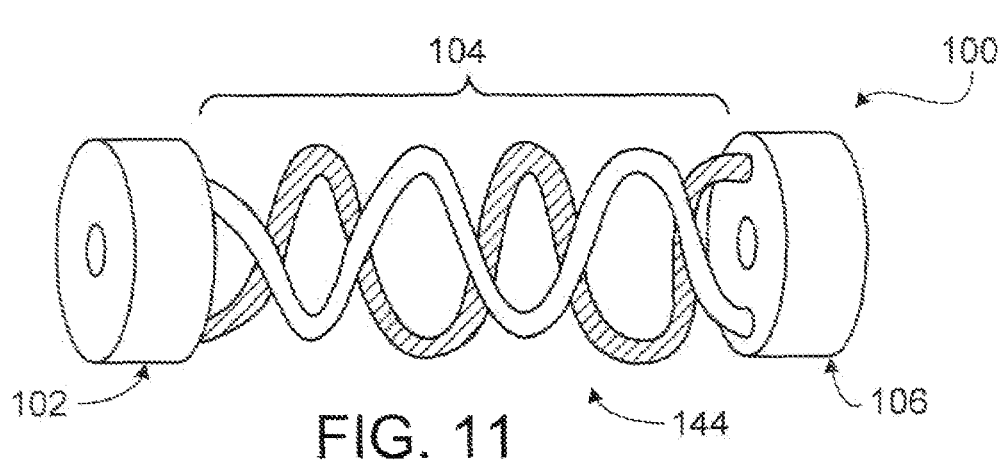

In the implementations described thus far, the extensor segment 104 is a single straight tube connecting the anchor segments 102, 106. In other implementations, as shown in FIG. 10, the extensor segment 104 includes multiple ligaments 138, 140, 142, each of which is an independently actuable extensor. The multiple ligament implementation of FIG. 10 enables the annelid 100 to conform closely to the vessel anatomy. For example, if one were to elongate some, but not all, of the ligaments, the annelid 100 would curve. This is useful for crawling through a curved vessel. In some implementations, the individual ligaments 138, 140, 142 each have a series of individually actuable extensor sub-segments to allow the user to better control movement of the annelid 100 within the vessel. In FIG. 11, the extensor segment 104 features one or more ligaments wound in a helix 144. The resulting helix 144 also allows the user to better control movement of the annelid 100 within the vessel. The helix 144 causes the annelid 100 to twist as it moves within the vessel.

Figure 12:
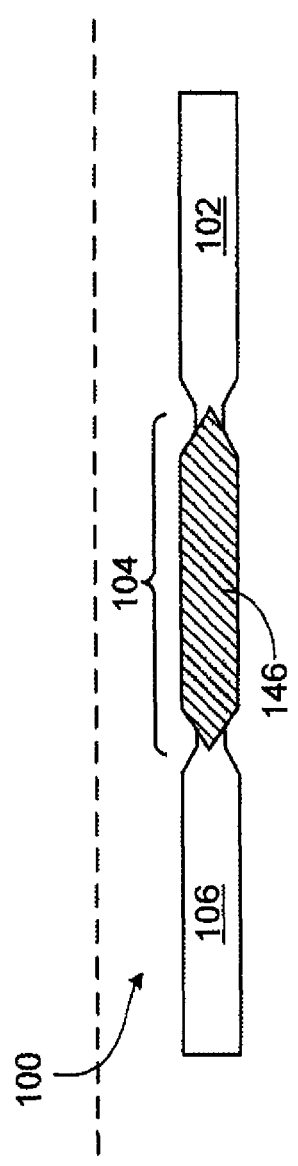
FIGS. 12-14 show an agent affixed to the annelid.
Figure 13:
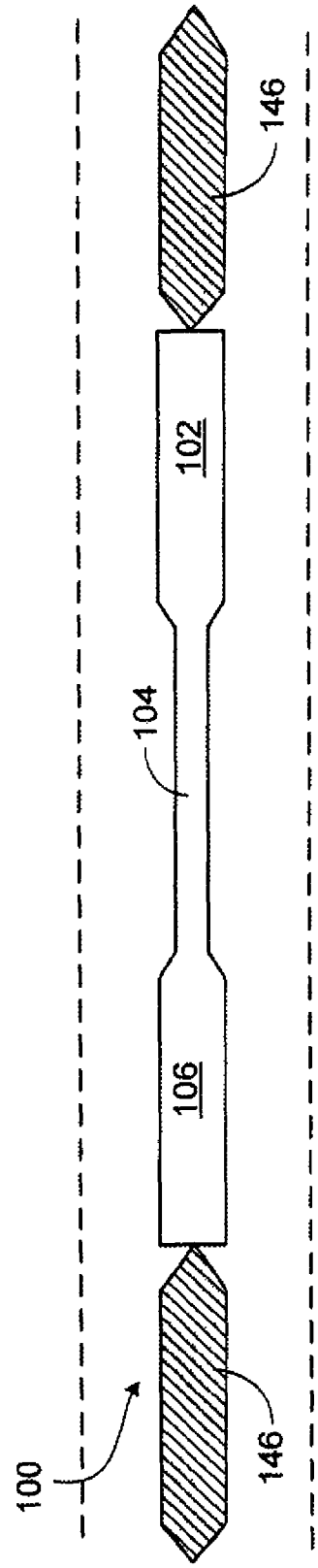
Figure 14:
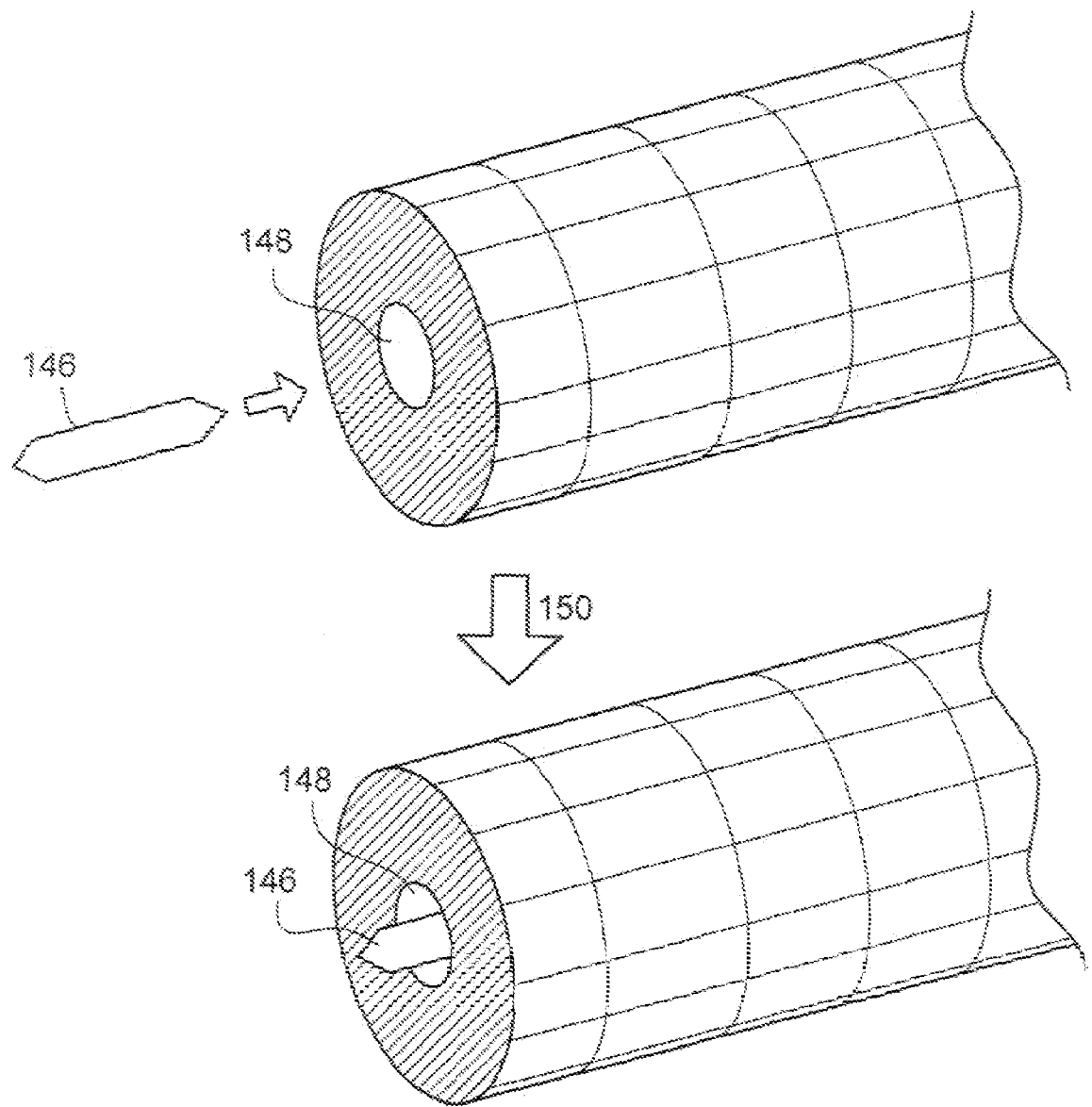

In the example of FIGS. 12-13, an agent 146 is affixed to the annelid 100 for delivery to a particular location. The agent is affixed either along the extensor segment 104, or to one or both anchor segments 102, 106. One way to engage the agent 146 is to insert the agent into a hole 148 in the anchor segment 102, 106. The hole 148 includes a separately actuable agent-holding EAP. When actuated, as shown in FIG. 14, the anchor segment clamps down (150) on the agent 146. The agent 146 can then be delivered through the vessel to the desired location within the body. When the annelid 100 delivers the agent 146 to the desired location, the anchor segment 102, 106 is deactuated, thereby relaxing its grip on the agent 146 and causing the agent's release into the vessel.

In some implementations, the annelid 100 can be used in conjunction with other annelids 100. For example, two or more annelids can be arranged in sequence.

Other embodiments are within the scope of the following claims.

The invention claimed is:

1. An apparatus for delivery of a medical device through a vessel, the apparatus comprising:
   an extensor segment configured to be selectively elongated along a longitudinal axis of the apparatus;
   first and second anchor segments positioned on either side of the extensor segment and fixedly secured to opposing ends of the extensor segment, the first and second anchor segments configured to be selectively radially expanded and place a compressive load against the vessel; and
   a medical device affixed along the extensor segment between the first and second anchor segments, wherein the medical device is selected from the group consisting of a stent, a balloon, a graft, and a filter;
wherein each segment has associated with it an individually-addressable electro-active polymer;
wherein the first and second anchor segments each include a plurality of holes extending axially therethrough;
wherein the medical device is removable from the extensor segment such that the medical device remains in the vessel when the apparatus is withdrawn.

2. The apparatus of claim 1, further comprising:
a power source coupled to provide electrical current to actuate the electro-active polymer of each segment.

3. The apparatus of claim 1, further comprising:
a controller configured to direct a control signal to cause actuation of the electro-active polymer associated with a segment.

4. The apparatus of claim 1, wherein the electro-active polymer comprises a polypyrrole polymer.

5. The apparatus of claim 1, wherein the electro-active polymer associated with at least one of the first and second anchor segments comprises an individually-addressable radially-actuating electro-active polymer.

6. The apparatus of claim 1, wherein the electro-active polymer associated with the extensor segment comprises an individually-addressable length-actuating electro-active polymer.

7. The apparatus of claim 1, further comprising a pair of electro-active polymer fingers configured to form a fork in response to actuation.

8. The apparatus of claim 1, wherein the extensor segment comprises a series of sub-segments, wherein each sub-segment has associated with it an individually-addressable electro-active polymer.

9. The apparatus of claim 1, wherein the extensor segment comprises plural ligaments, wherein each ligament has associated with it an individually-addressable electro-active polymer.

10. The apparatus of claim 1, wherein at least one of the first and second anchor segments comprises a pair of individually-addressable electro-active sides configured to change the orientation of the at least one of the first and second anchor segments in response to actuation.

11. The apparatus of claim 1, wherein the extensor segment comprises plural individually addressable ligaments wound in a helix.

12. The apparatus of claim 1, wherein at least one of the segments includes a radio-opaque material.

13. The apparatus of claim 1, further comprising:
an external power source electrically coupled to the segments.

14. The apparatus of claim 13, wherein the electric coupling comprises an inductive coupling.

15. The apparatus of claim 1, further comprising:
a battery electrically coupled to the segments.

16. A method of delivering a medical device through a vessel, the method comprising:
affixing a medical device to a delivery apparatus, the delivery apparatus having a first anchor segment configured to be selectively radially expanded, a second anchor segment configured to be selectively radially expanded, and an extensor segment extending between the first and second anchor segments and fixedly secured to each of the first and second anchor segments which is configured to be selectively elongated, wherein each segment has associated with it an individually-addressable electro-active polymer, wherein the medical device is affixed along the extensor segment between the first and second anchor segments, wherein the medical device is selected from the group consisting of a stent, a balloon, a graft, and a filter, and wherein the first anchor segment and the second anchor segment each include a plurality of holes extending axially therethrough;
inserting the delivery apparatus into the vessel;
actuating the delivery apparatus within the vessel to propel the apparatus to a target location within the vessel, wherein the step of actuating the delivery apparatus further comprises:
radially expanding the first anchor segment to exert a compressive load against the vessel thereby securing the first anchor segment within the vessel;
elongating the extensor segment;
radially expanding the second anchor segment to exert a compressive load against the vessel thereby securing the second anchor segment within the vessel;
releasing the first anchor segment from the vessel; and
contracting the extensor segment;
releasing the medical device from the delivery apparatus at the target location within the vessel; and
withdrawing the delivery apparatus from the vessel, wherein the medical device remains at the target location.

17. The method of claim 16, further comprising:
steering the apparatus within the vessel.

18. The method of claim 16, further comprising:
extending a first side of one of the anchor segments while contracting a second side of the one of the anchor segments.

19. The method of claim 16, further comprising:
controlling the speed of propulsion.

20. The method of claim 16, further comprising:
controlling the direction of propulsion.

* * * * *